United States Patent [19]

Dittrich et al.

[11] Patent Number: 5,437,775
[45] Date of Patent: Aug. 1, 1995

[54] METHOD FOR PREPARING HIGH-PURITY PROPYLENE CARBONATE AND FOR SIMULTANEOUSLY MAKING PASSIVATED ELECTRODES

[75] Inventors: Wolfgang Dittrich, Munich; Herbert Hill, Erding; Elke Kinzel, Zorneding, all of Germany

[73] Assignee: Huls Aktiengesellschaft, Marl, Germany

[21] Appl. No.: 30,114

[22] Filed: Jan. 12, 1994

[30] Foreign Application Priority Data

Sep. 10, 1990 [DE] Germany .......... 40 28 708.4

[51] Int. Cl.⁶ ............................. B01D 17/06
[52] U.S. Cl. ........................ 204/186; 204/140
[58] Field of Search ............ 204/130, 131, 222, 59 R, 204/186, 140

[56] References Cited

U.S. PATENT DOCUMENTS

| | | | |
|---|---|---|---|
| 3,444,062 | 4/1966 | Felici et al. | 204/131 |
| 3,796,646 | 3/1974 | Zambon | 204/222 |
| 5,183,543 | 2/1993 | Toyosawa et al. | 204/242 |

FOREIGN PATENT DOCUMENTS

| | | | |
|---|---|---|---|
| 928820 | 6/1963 | United Kingdom . | |
| 1177392 | 9/1985 | U.S.S.R. | 204/131 |

Primary Examiner—John Niebling
Assistant Examiner—Kishor Mayekar
Attorney, Agent, or Firm—Louis M. Heidelberger; Reed Smith Shaw & McClay

[57] ABSTRACT

This invention relates to a method for preparing high-purity propylene carbonate and for simultaneously making passivated electrodes, wherein optionally prepurified propylene carbonate is exposed in a cell to an electric field between bare electrodes.

30 Claims, 4 Drawing Sheets

METHOD FOR PREPARING HIGH-PURITY PROPYLENE CARBONATE AND FOR SIMULTANEOUSLY MAKING PASSIVATED ELECTRODES

FIELD OF THE INVENTION

The present invention relates to a method for preparing high-purity propylene carbonate and for simultaneously making passivated electrodes.

BACKGROUND OF THE INVENTION

Propylene carbonate (4-methyl-1,3-dioxolane-2-one) is a colorless, aprotic solvent with a relatively high dielectric constant. It is widely used as a solvent for various synthetic polymers and as a reaction medium. Propylene carbonate is chiefly used as a non-aqueous solvent for electrolytes for high-energy batteries.

As a dielectric, propylene carbonate is generally suited for use in electrostatic apparatus. High energy or power densities can be attained in electrostatic apparatus when high electric fields are maintained at small injection or leakage currents within the dielectric used. The electric conductivity of commercial propylene carbonate which lies normally between $10^{-6}$ and $10^{-7}$ S/cm is however too high and thus not in a position to reduce leakage currents to a considerable extent. As a consequence, it cannot be used in an unpurified or only coarsely purified state.

The major impurities found in commercial propylene carbonate are propylene oxide, carbon dioxide, 1,2- and 1,3-propanediol (propylene glycol), allyl alcohol, ethylene carbonate, sodium ions, reaction products of tetramethyl ammonium bromide, water and other unidentified substances. The methods employed for determining these impurities, e.g. GC, IC or MS, are very troublesome.

SUMMARY OF THE INVENTION

Various methods of purifying propylene carbonate are known. For instance, in "Pure and Applied Chem. 27", (1971), pp. 275–280, and in "Recommended Methods for Purification of Solvents and Tests for Impurities", Ed. J. F. Coetzel, Pergamon Press (1982) pp. 19–24, T. Fujinaga and K. Izutsu describe a fractional distillation under reduced pressure which may be followed by an evaporation process in which the content of low-boiling organic components may be reduced to less than 0.4 ppm and the water content to less than 1.5 ppm. The glycol concentration, however, does not change. In these methods a propylene carbonate with a conductivity of about $10^{-7}$ to $10^{-8}$ S/cm is obtained.

Prior to the fractional distillation a drying operation may be carried out with the aid of molecular sieves, with activated alumina or dried calcium oxide (Y. Mary, Revue de Chim. Minerale 13 (1978), p. 185 and L. M. Mukherjee, CRC Crictical Rec. in Anal. Chem. 77 (1971), p. 345).

Alternatively, a chemical prepurification step may be carried out with potassium permanganate. In such a step $MnO_2$ is precipitated and the excessive $KMnO_4$ is destroyed by heating at 120° C. A vacuum distillation is subsequently carried out.

Electrodialysis membranes can also be used for purifying propylene carbonate (Influence de la pureté du carbonate de propylène sur sa résistivité électrique, A. Denat, B. Gosse and J. P. Gosse, Journal de chimie physique, 1975, 72, No. 3, pp. 343–346).

Electrodialysis membranes, however, have the following disadvantages: They are destroyed during electric breakdowns that cannot be ruled out in electrostatic apparatus, i.e. they stick together. In many cases they exhibit a non-uniform quality, which creates problems during operation of the electrostatic apparatus. Moreover, covering of the uneven electrode surfaces with membranes necessitates very great constructional efforts. Electrodialysis membranes are in general not designed-for high voltages. They are normally used in the volt range only. Purification or deionizaton of propylene carbonate is not always satisfactory because an increased water content is present in the propylene carbonate because of the storing of the membranes in aqueous solution after the drying thereof or the transfer into an organic solvent.

It is already known that liquids are subjected to an electric field at small field strenghts by using electrodes. For instance A. Nikuradse (offprint from Isolieröle, edited by Rhenania-Ossag Mineralölwerke AG; Hamburg, Julius Springer, Berlin, 1937) describes the electric conduction in insulating oils. F. Wollers, "Injectionsstrom und Laufzeitmessung in flüssigem Benzol", thesis 1971, describes the time course of the current at small field strengths directly after application of a direct voltage for metal electrodes in liquid benzene. Benzene, however, is not suited as a dielectric in electrostatic apparatus, among other things, because of its very low dielectric constant.

It is the object of the present invention to provide a reliable method for purifying propylene carbonate wherein propylene carbonate with an adequately reduced conductivity is obtained, so that it is suited for use as a dielectric in electrostatic apparatus.

This object is attained with a method as specified in the patent claims.

DESCRIPTION OF THE PREFERRED EMBODIMENTS

Surprisingly enough, the method of the invention effects a drastic reduction of the conductivity of propylene carbonate and a simultaneous passivation of the electrodes. Both the electrode which is obtained in accordance with the invention and the propylene carbonate which is also obtained with the aid of the invention and has a conductivity ranging from $10^{-10}$ to $10^{-14}$ S/cm are suited for use in electrostatic apparatus.

Leakage currents are considerably reduced due to propylene carbonate having a reduced conductivity. The advantage of the passivated electrodes during use in electrostatic apparatus must be seen in their increased breakdown strength and their reduced injection capability which, in turn, leads to smaller leakage currents. On the whole, the electrostatic apparatus can thus be used immediately and at full power.

It is assumed that the method of the invention effects, e.g., an ionic dissociation of the impurities of the propylene carbonate. In this process the ions discharge or deposit on the electrodes, i.e. a dissociation current is inter alia created. With a stagnant liquid, the current integral correlates with the initially existing ionic impurities in the propylene carbonate. The dissociation velocity generally rises with the electric field, but may differ in response to the substances respectively used. The current curve may be recorded by means of a storage oscillograph or by means of a mechanical recorder.

The electrodes are passivated in the method of the invention at the same time, with the purification of the propylene carbonate being the more efficient, the more the passivation of the electrodes advances.

In the present invention, "bare" electrodes means commercial, unused electrodes which are polished prior to use, purified and dried. They are normally polished with the aid of a polishing stone, purified in the ultrasonic bath with water and acetone and dried under vacuum; they exhibit a surface roughness of less than 30 $\mu$m.

In the present invention "passivation" of the electrodes means a change in the surface of the electrodes which may be of a chemical and/or physical nature. The mechanism of this passivation has not been completely clarified yet. It is however assumed that in the method of the invention a coat layer is formed on the electrodes and/or that a surface layer is removed. A decisive criterion of an existing passivation is the considerable decrease in injection currents when passivated electrodes are used in an electrostatic device.

Figure 1:
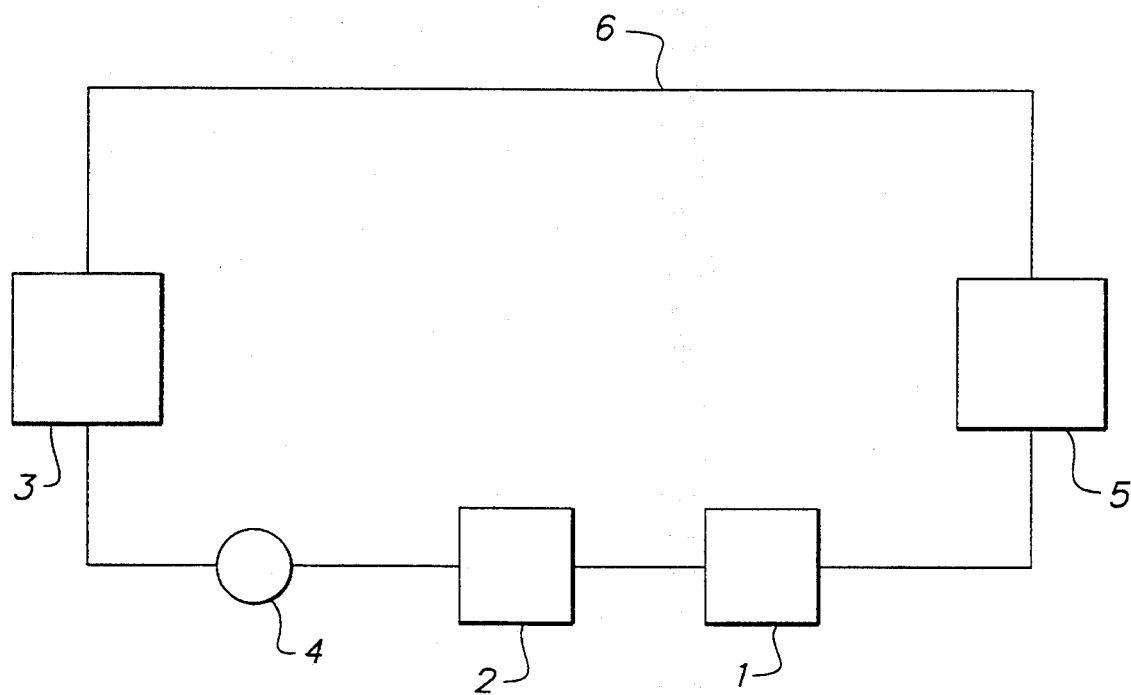
FIG. 1 is a schematic representation of the inventive method carried out in a purifying cell in circulatory fashion.

FIG. 1 is a schematic representation of the inventive method carried out in a purifying cell in circulatory fashion.

Figure 2:
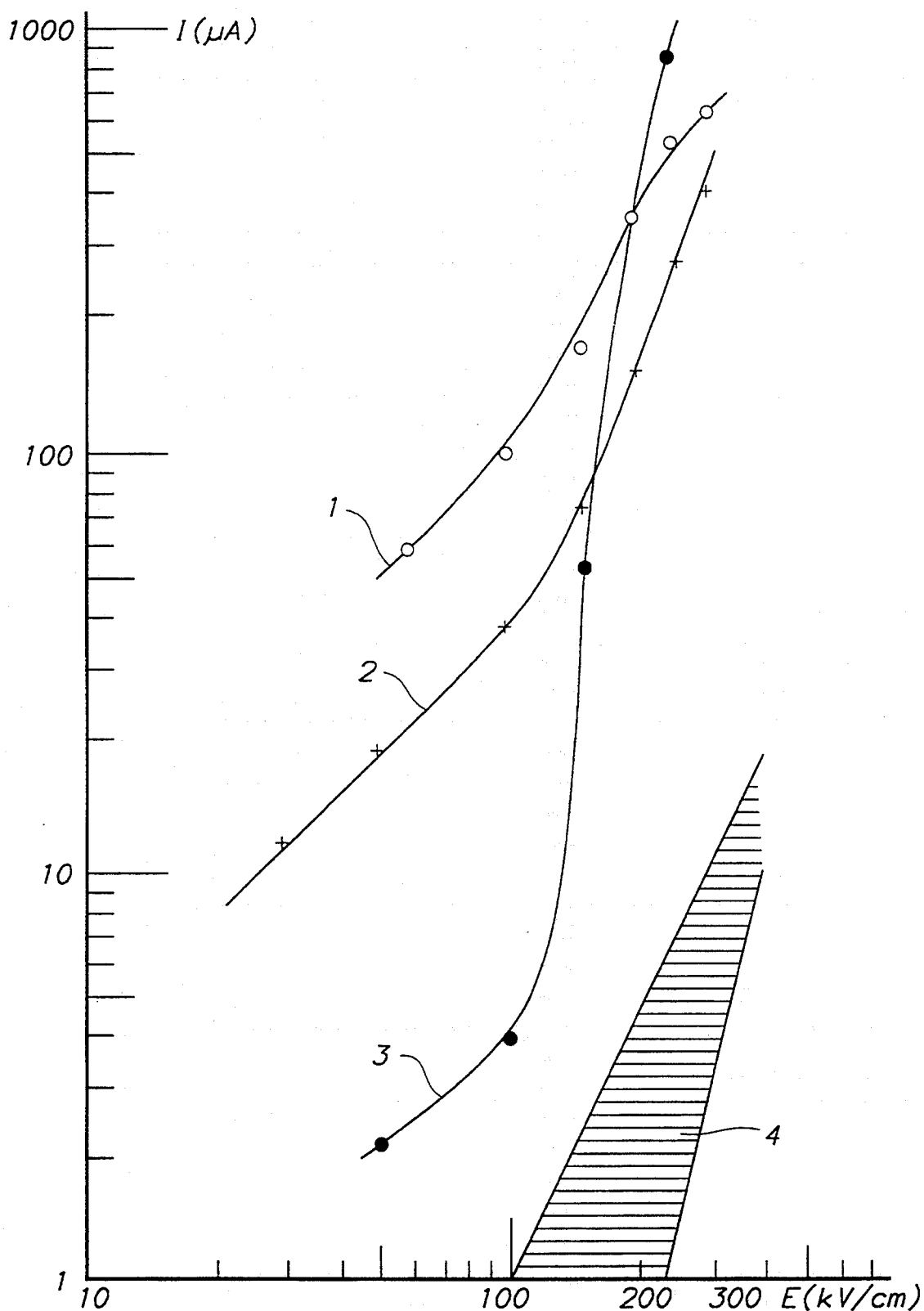
FIG. 2 is a diagram showing the relation between the injection current and the field strength in a purifying cell when propylene carbonate is used.

FIG. 2 is a diagram showing the relation between the injection current and the field strength in a purifying cell when propylene carbonate is used.

Figure 3:
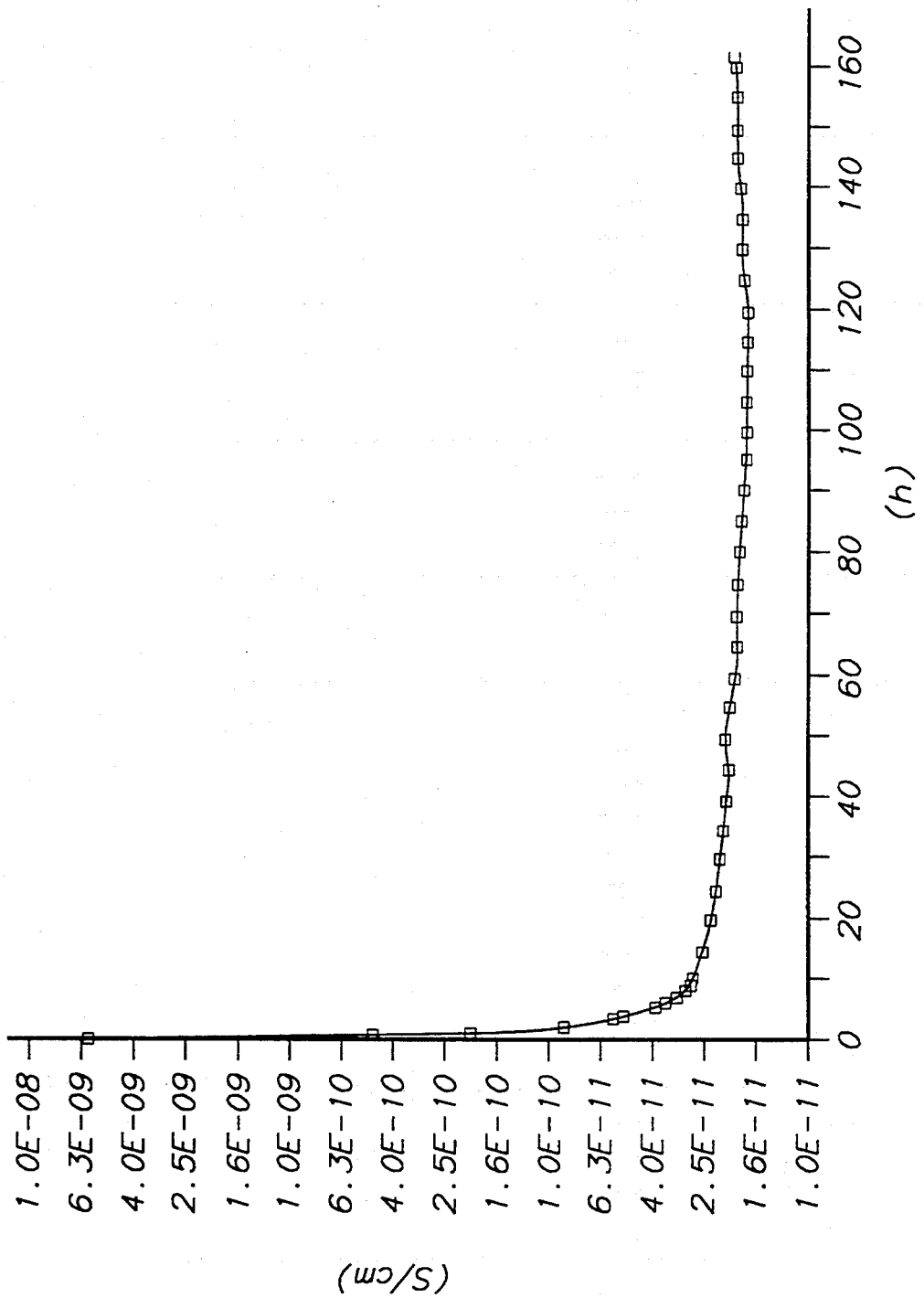
FIG. 3 illustrates the decrease in conductivity of propylene carbonate as a function of time at a field strength of 20 kV/cm.

FIG. 3 illustrates the decrease in conductivity of propylene carbonate as a function of time at a field strength of 20 kV/cm.

Figure 4:
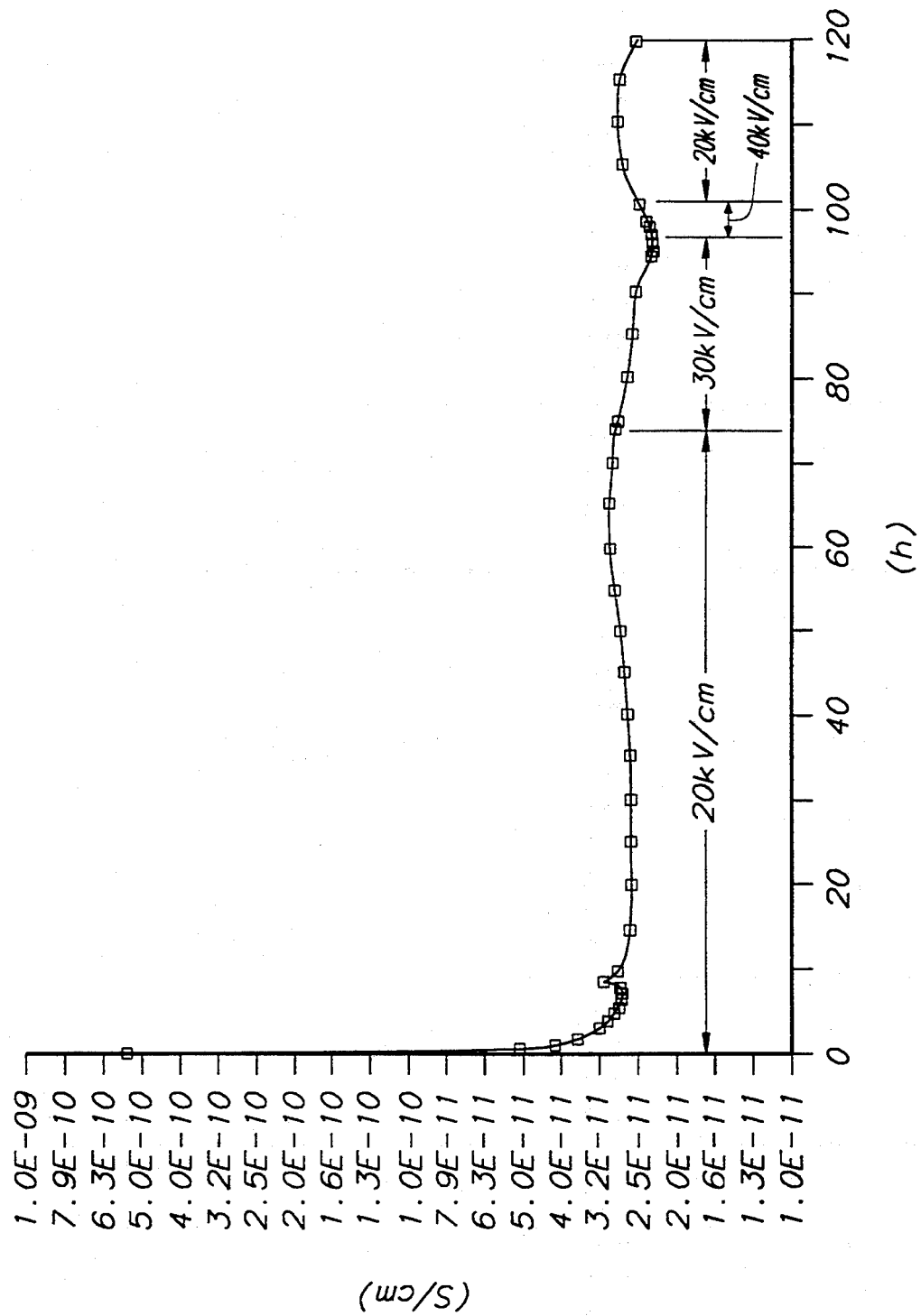
FIG. 4 illustrates the decrease in conductivity of propylene carbonate as a function of time and at a variable field strength.

FIG. 4 illustrates the decrease in conductivity of propylene carbonate as a function of time and at a variable field strength.

In a first embodiment, the method of the invention may be performed in a simple purifying cell from which the purified propylene carbonate is later taken for storing purposes.

In a second embodiment, however, the resultant propylene carbonate is preferably transferred into a part of an electrostatic aparatus in which the method of the invention, i.e. the purification step, is continued, or the method of the invention is directly carried out in an electrostatic apparatus.

The two embodiments of the invention shall now be described in more detail.

If a purifying cell is used, it is preferred that the propylene carbonate circulates through the cell. Usually, this takes place at room temperature and under normal pressure. An inert atmosphere, in particular a nitrogen atmosphere, is preferred.

When the method of the invention is performed in practice, the dissociation velocity of the ionic compounds of the propylene carbonate is preferably determined first, namely in dependence upon the electric field strength. As shown in FIG. 1, an electric field is created in a test cell 1 above a stagnant liquid consisting of propylene carbonate, whereby a dissociation current is inter alia created. The time which is needed until the dissociation current is approximately zero is the minimum purification time required for purifying the propylene carbonate in the purifying cell 2. The prepurified propylene carbonate is now passed from a supply container 3 via a pump 4 into the purifying cell 2 in which it is treated in accordance with the method of the invention, and further into a reception container 5.

Instead of reception container 5, it may be directly passed into an electrostatic apparatus. Containers 3 and 5 are connected to an equalizing conduit 8 to permit repeated passage through purifying cell 2, or the circulation of propylene carbonate through the purifying cell already during the purifying operation. Undesired deposits on the electrodes can be prevented owing to the relative velocity achieved thereby between the flowing propylene carbonate and the fixed electrodes. This can also be accomplished in that at least one electrode is kept in motion. The purification quality of the propylene carbonate can be constantly checked with the aid of test cell 1 which is arranged after purifying cell 1. The atmosphere above the containers consists of a highly pure inert gas, such as nitrogen or noble gases.

The method is preferably carried out with a DC field.

Commercial metal electrodes, metal-coated electrodes of plastics or ceramics may be used as electrodes. Examples of metal electrodes are brass or platinum electrodes.

The electric field may be temporally controlled as to its height. An occasional, non-periodic change in polarity of the applied voltage, e.g. pole reversal of the field, is preferred. Field strengths of at least 1 kV/cm, preferably 10 to 100 kV/cm, are normally applied; field strenghts of 15 to 20 kV/cm are especially preferred.

The current density of the current existing during purification may be limited upwards, preferably to values of less than 30 $\mu$A/cm$^2$.

The electrodes used in the purifying cell are preferably of mushroom shape, i.e. they are provided with rounded edges. The electrode surface has e.g. a size of 1 to 5000 cm$^2$, in particular 10 to 100 cm$^2$. The electrode spacing is preferably 0.5 mm to 6 cm, in particular 1 mm to 1 cm, with 4 to 6 mm being aspecially preferred.

The throughput of dielectric normally lies between 0.4 and 1.5 l/min.

If the method of the invention is carried out in accordance with the second embodiment in an electrostatic apparatus, such as a pulse generator equipped with stator and rotor electrodes or a capacitor—optionally after a purifying operation has already been carried out in the purifying cell, it may be performed under the same conditions as described above for the purifying cell. In this case, however, the following changes are expedient:

The method of the invention is preferably carried out in the pulse generator at temperatures ranging from 0° to 10° C. and at a pressure of 400 to 600 kPa. Shell-shaped titanium or brass electrodes, which have e.g. an electrode surface of 19 to 250 cm$^2$, are preferably used as metal electrodes. A preferred speed of the rotor is between 1000 and 7500 r.p.m. The smallest distance between the electrodes lies at 0.5 to 2 mm, preferably at 1 mm. The electric field strength is at least 50 kV/cm, preferably 100 to 330 kV/cm, with 200 to 310 kV/cm being especially preferred.

The propylene carbonate is purified more rapidly at higher field strengths, which normally exist in a pulse generator, than at lower field strengths, as occur e.g. in the purifying cell. For instance, 1 l of propylene carbonate is purified in the pulse generator at 150 kV/cm for 10 to 15 minutes, whereas 12 hours are needed in the purifying cell at 20 kV/cm, so as to obtain a propylene carbonate with a conductivity of $5 \times 10^{-11}$ S/cm in each case.

As illustrated in FIG. 2, currents are considerably reduced in a cell due to the excellent passivation of the electrodes when propylene carbonate with a conductivity of $1 \times 10^{-11}$ to $2 \times 10^{-11}$ S/cm is used. The applied voltage amounted here to 20 kV, and the electrode spacing was 1 mm.

Curves 1 through 3 show the currents obtained at specific field strengths and by means of bare electrodes for propylene carbonate which has been prepurified with the aid of electrodialysis membranes and exhibits a conductivity of $9 \times 10^{-11}$ S/cm (curve 1), $6 \times 10^{-11}$ S/cm (curve 2) and $5 \times 10^{-12}$ S/cm (curve 3). By contrast, region 4 shows measured currents as are obtained in the case of propylene carbonate having a conductivity of $1 \times 10^{-11}$ to $2 \times 10^{-11}$ S/cm with the aid of passivated electrodes.

FIGS. 3 and 4 show how the conductivity values of the propylene carbonate decrease in the method of the invention. As illustrated in FIG. 3, the initial conductivity of the prepurified propylene carbonate amounted to about $6 \times 10^{-9}$ S/cm and could be reduced through the inventive method to about $2.8 \times 10^{-11}$ S/cm after about 10 h by applying a voltage of 10 kV and by using bare brass electrodes with a spacing of 0.5 cm. 2 l of propylene carbonate were circulated. 90 h after the voltage had been cut off, a conductivity value of about $10^{-10}$ S/cm could be observed. The conductivity could thus be reduced approximately 100 times.

FIG. 4 illustrates another example in which propylene carbonate was purified with the aid of bare brass electrodes and at varying voltages (10, 15, 20, 10 kV). The conductivity could here be reduced from about $5 \times 10^{-10}$ to about $3 \times 10^{-11}$ S/cm.

The propylene carbonate used can be prepurified in the known way, e.g. through reaction with potassium permanganate and subsequent vacuum distillation.

The method of the invention as such can also be carried out with other polar dielectrics having a dielectric constant of more than 20. Especially cyclic carbonates, such as butylene carbonate, chloroethylene carbonate or mixtures thereof, acid amides, such as N-methyl-2-pyrrolidone, N-methyl formamide, N-methyl acetamide, N-methyl propionamide, or N,N-dimethyl formamide, alcohols, such as methanol, ethanol, propanol or 1,2-propylene glycol, acetonitrile and dimethylsulfoxide, are suitable dielectrics.

The following examples are illustrative of the invention.

Example 1

4 l of commercial propylene carbonate with a conductivity of about $2 \times 10^{-7}$ S/cm are stirred with an excess of potassium permanganate (15 g/l propylene carbonate) for 8 h. A filtering operation is subsequently carried out with the aid of a folded filter and 2 l of the still violet-colored solution are respectively purified in a nitrogen atmosphere on a column which is filled with alumina (neutral, activity 1, 600 g/2 l propylene carbonate) and has a diameter of 5 cm. Propylene carbonate with a conductivity of about $1 \times 10^{-8}$ S/cm is here obtained.

The propylene carbonate is subsequently subjected to a rapid vacuum distillation at a pressure of 100 Pa. The first fraction of about 500 ml is rejected as first runnings, and the next fraction of about 2 l propylene carbonate with a specific conductivity of about $5 \times 10^{-10}$ S/cm is further purified by means of a high voltage. To this end, propylene carbonate is circulated by means of a pump and in a nitrogen atmosphere for 24 h through a purifying cell which comprises bare brass electrodes and has high voltage applied thereto. The electric field strength is 20 kV/cm, the electrode spacing 0.5 cm and the electrode surface 15 cm. The resultant propylene carbonate has a conductivity of about $10^{-11}$ S/cm.

Example 2

Brass electrodes with an electrode surface of 15 cm² are polished, purified in an ultrasonic bath with water and acetone and dried in vacuum. After the electrodes have been installed in a purifying cell, the electrode spacing is set to 5 mm and the cell is integrated into a circuit comprising a pump and a propylene carbonate supply flask.

Like in Example 1, 500 ml of prepurified propylene carbonate are pumped through the cell at room temperature and under normal pressure in a nitrogen atmosphere at a rate of 0.75 l/min. High voltage is applied to the cell. At a maximum current of 100 µA, the voltage is increased up to a final voltage of 10 kV. The electric field strength is 20 kV/cm. The propylene carbonate is pumped through the cell for 12 h, whereby the electrodes are passivated. The resultant propylene carbonate has a conductivity of $2 \times 10^{-11}$ S/cm.

Example 3

4 l of commercial propylene carbonate with a conductivity of about $2 \times 10^{-7}$ S/cm are stirred with an excess of potassium permanganate (15 g/l propylene carbonate) for 8 hours. A filtering operation is subsequently carried out by means of a folded filter and 2 l of the still violet-colored solution are respectively purified in a nitrogen atmosphere on a column (neutral, activity super 1, 300 g/2 l propylene carbonate) which is filled with alumina and has a diameter of 5 cm. Propylene carbonate with a conductivity of $4 \times 10^{-9}$ S/cm is here obtained.

The propylene carbonate is subsequently subjected to a rapid vacuum distillation at a pressure of 100 Pa. The first fraction of about 500 ml is rejected as first runnings, and the next fraction of about 2 l of propylene carbonate with a specific conductance of $5 \times 10^{-10}$ S/cm is then purified in a purifying cell in circulation by means of two bare brass electrodes at a field strength of 20 kV/cm for 4 days. 1.5 l propylene carbonate are then filled with postpurified nitrogen into a pulse generator having brass electrodes with a surface of 19 cm².

Propylene carbonate is pumped through the pulse generator in a cooled circulatory system at a pressure of 550 kPa and a throughput of 1 l/min at a speed of 2,000 r.p.m. At the beginning of the test the propylene carbonate temperature amounts to 5° C. and at the end to 31° C. The existing field strength is 100 kV/cm for 3 min, 150 kV/cm for 3 min, 200 kV/cm for 3 min and 220 kV/cm for 5 min.

The conductivity of the propylene carbonate before the purification step in the pulse generator amounts to $6 \times 10^{-11}$ S/cm. It amounts to $2.5 \times 10^{-12}$ S/cm after the electrical purification step at the above-mentioned field strengths for 14 min.

At the same initial conductivity, another propylene carbonate filling of the same quality would yield a conductivity of $2.5 \times 10^{-12}$ S/cm after 2 min of electrical purification in the pulse generator at 2,000 r.p.m. and at a field strength of 180 kV/cm.

Example 4

2 l of commercial propylene carbonate with a conductivity of about $2 \times 10^{-7}$ S/cm are stirred with an excess of potassium permanganate (15 g/l) for 8 h. Filtration is subsequently carried out by means of a folded filter. The still violet-colored solution is now purified in a nitrogen atmosphere on a column which is filled with alumina (neutral, Woelm, activity super 1, 300 g/2 l propylene carbonate) and has a diameter of 3 cm. A propylene carbonate with a conductivity of $2 \times 10^{-8}$ S/cm is then obtained.

The propylene carbonate is subsequently subjected to a rapid vacuum distillation. The first fraction of approximately 500 ml is rejected as first runnings, and 500 ml of the next fraction are filled into a pulse generator in a nitrogen atmosphere and purified.

At the beginning of the test, the propylene carbonate temperature is 0° C. and at the end 35° C. The pressure is at 500 kPa, and the speed of the pulse generator amounts to 1,800 r.p.m. The existing field strength is 100 kV/cm for 4 min, 160 kV/cm for 3 min, 230 kV/cm for 3 min, 275 kV/cm for 3 min and 310 kV/cm for 5 min. Titanium is used as rotor material, and brass as stator material. The electrode surface amounts to 19 cm².

Prior to the electrical purification in the pulse generator, the conductivity of the propylene carbonate is $1.5 \times 10^{-10}$ S/cm, and after 17 min of electrical purification it amounts to $4 \times 10^{-12}$ S/cm at the predetermined field strengths.

At the same initial conductivity, another propylene carbonate filling of the same quality would yield a conductivity of $3.6 \times 10^{-12}$ S/cm after an electrical purification operation has been carried out in the pulse generator at 2,500 r.p.m. and at a field strength of 250 kV/cm for 2.5 min.

We claim:

1. A method for preparing high-purity propylene carbonate, said method comprising the steps of:
   (a) exposing in a cell prepurified propylene carbonate liquid to an electric field of at least 1 kV/cm between first and second bare metal electrodes for a time to obtain a high-purity propylene carbonate; and
   (b) simultaneously passivating said first and second electrodes.

2. The method of claim 1 which further comprises the step of (c) circulating said exposed propylene carbonate through said cell.

3. The method of claims 1 or 2 which further comprises the step of (d) moving at least one of said first and second electrodes.

4. The method of claim 3 wherein said electric field is a DC field.

5. The method of claim 4 wherein said method is carried out at room temperature and under normal pressure.

6. The method of claim 5 wherein said method is carried out in an inert atmosphere.

7. The method of claim 5 wherein said method is carried out in a nitrogen atmosphere.

8. The method of claim 6 wherein said electrodes are brass electrodes.

9. The method of claim 6 wherein said electrodes are titanium electrodes.

10. The method of claim 4 which further comprises the step of (e) varying said field strength as a function of time.

11. The method of claim 10 which further comprises the step of (f) limiting upwardly the current density generating during step (a).

12. The method of claim 11 wherein said current density is smaller than 30 kV/cm².

13. The method of claim 12 wherein said electrodes are cylindrical-shaped.

14. The method of claim 12 wherein said electrodes are mushroom-shaped.

15. The method of claim 13 wherein said electrodes are spaced at from about 0.5 mm to about 60 mm.

16. The method of claim 15 wherein said electrodes have a surface of from about 1 to about 5000 cm².

17. The method of claim 11 wherein said cell comprises an electrostatic apparatus.

18. The method of claim 17 wherein said electrostatic apparatus is a pulse generator.

19. The method of claim 17 wherein said electrostatic apparatus is a capacitor.

20. The method of claim 18 wherein said the strength of said electric field is at least 50 kV/cm.

21. The method of claim 20 wherein said electrodes have a minimum spacing of from about 0.5 mm to about 2 mm.

22. The method of claim 21 which further comprises the step of (g) changing the polarity of said electric field.

23. The method of claim 22 which further comprises the step of (h) operating said pulse generator at a rotational speed of from about 1000 rpm to about 7500 rpm.

24. The method of claim 1 wherein said propylene carbonate is prepurified by reaction with potassium permanganate.

25. The method of claim 1 wherein said propylene carbonate is prepurified by vacuum distillation.

26. The method of claim 7, wherein said electrodes are brass electrodes.

27. The method of claim 14 wherein said electrodes are titanium electrodes.

28. The method of claim 14 wherein said electrodes are spaced at from about 0.5 mm to about 60 mm.

29. The method of claim 28 wherein said electrodes have a surface of from about 1 to about 5000 cm².

30. The method of claim 19 wherein the strength of said electric field is at least 50 kV/cm.

* * * * *